(12) United States Patent
Cho et al.

(10) Patent No.: US 9,488,566 B2
(45) Date of Patent: Nov. 8, 2016

(54) CENTRIFUGAL FORCE-BASED MICROFLUIDIC DEVICE AVAILABLE FOR RELIABILITY VERIFICATION, AND ANALYZING METHOD USING THE SAME

(75) Inventors: Yoon-Kyoung Cho, Ulsan (KR); Ji-Woon Park, Ulsan (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 1110 days.

(21) Appl. No.: 13/358,214

(22) Filed: Jan. 25, 2012

(65) Prior Publication Data

US 2013/0034912 A1 Feb. 7, 2013

(30) Foreign Application Priority Data

Aug. 3, 2011 (KR) .................. 10-2011-0077505

(51) Int. Cl.
| | |
|---|---|
| *G01N 21/07* | (2006.01) |
| *G01N 21/64* | (2006.01) |
| *G01N 21/76* | (2006.01) |
| *B01L 3/00* | (2006.01) |

(52) U.S. Cl.
CPC ......... *G01N 21/07* (2013.01); *B01L 3/502738* (2013.01); *B01L 3/502753* (2013.01); *G01N 21/6428* (2013.01); *G01N 21/76* (2013.01); B01L 3/50273 (2013.01); B01L 2200/0652 (2013.01); B01L 2200/0668 (2013.01); *B01L 2300/0806* (2013.01); *B01L 2300/0864* (2013.01); *B01L 2300/0867* (2013.01); *B01L* (Continued)

(58) Field of Classification Search
CPC ................. G01N 35/00069; B01L 3/5027
USPC .......................................... 436/172
See application file for complete search history.

(56) References Cited

U.S. PATENT DOCUMENTS 5,755,942 A * 5/1998 Zanzucchi ........... B01J 19/0093
204/452
7,157,049 B2 * 1/2007 Valencia et al. ............. 422/68.1
(Continued)

FOREIGN PATENT DOCUMENTS

| KR | 10-2010-0038007 | 4/2010 |
|---|---|---|
| KR | 10-2011-0064572 | 6/2011 |

OTHER PUBLICATIONS

Beom Seok Lee, Yang Ui Lee, Han-Sang Kim, Tae-Hyeong Kim, Jiwoon Park, Jeong-Gun Lee, Jintae Kim, Hanshin Kim, Wee Gyo Lee and Yoon-Kyoung Cho "Fully integrated lab-on-a-disc for simultaneous analysis of biochemistry and immunoassay from whole blood" Lab Chip, 2011, 11, 70-78.*

(Continued)

*Primary Examiner* — Christopher A Hixson
*Assistant Examiner* — Emily Berkeley
(74) *Attorney, Agent, or Firm* — Lex IP Meister, PLLC

(57) ABSTRACT

A centrifugal force-based microfluidic device for a multiplexed analysis and an analyzing method using the same are provided. The microfluidic device includes a platform and a microfluidic structure including a plurality of chambers formed within the platform, and valves positioned between the chambers. The microfluidic structure includes a sample separation chamber connected to a sample injection hole, and a plurality of reaction chambers accommodating two or more types of markers specifically reacting with different types of target materials, separately by type. At least one of the target materials is a standard material, and at least one of the markers is a standard marker specifically reacting with the standard material.

13 Claims, 17 Drawing Sheets

(52) U.S. Cl.
CPC ............... *2300/16* (2013.01); *B01L 2400/0409* (2013.01); *B01L 2400/0677* (2013.01); *Y10T 436/2575* (2015.01)

(56) References Cited

U.S. PATENT DOCUMENTS

2008/0290048 A1* 11/2008 Jaeggi ............... B01L 3/502746
                                                      210/782
2009/0053108 A1* 2/2009 Cho et al. ........................ 422/72
2010/0086925 A1* 4/2010 Lee et al. ......................... 435/6

OTHER PUBLICATIONS

Cho, Yoon-Kyoung, Fully Intergrated Immunoassays on a Disc, Bioelectronics, Biointerfaces, and Biomedical Applications 4, vol. 35, Issue7, May 1, 2011, Montreal, QC, Canada.

* cited by examiner

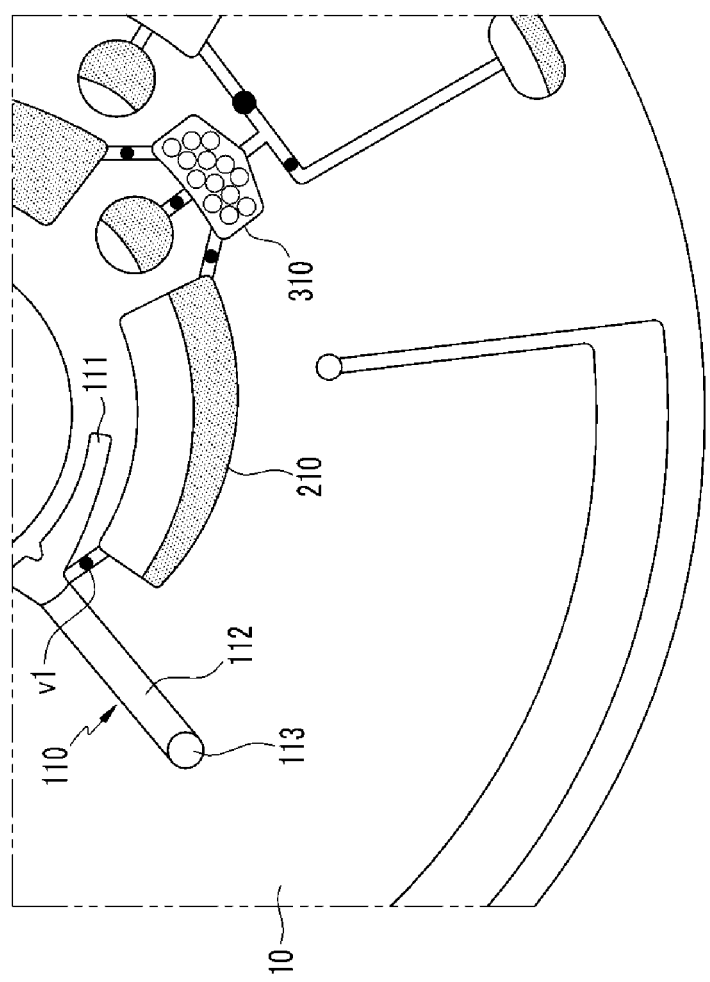

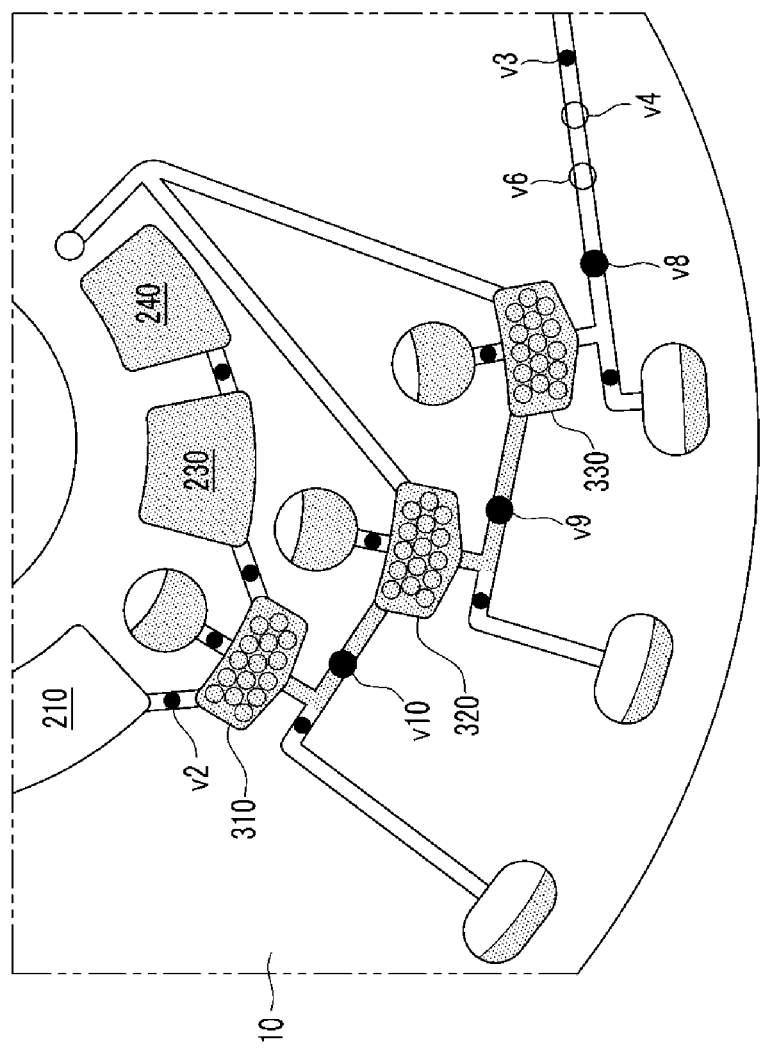

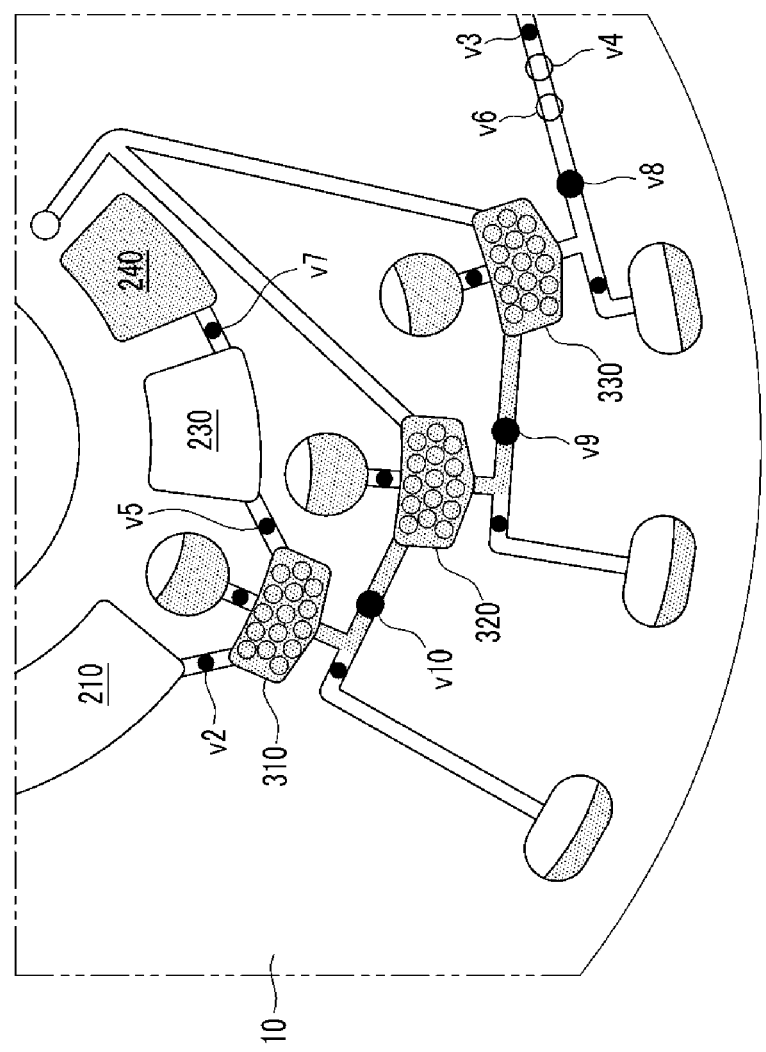

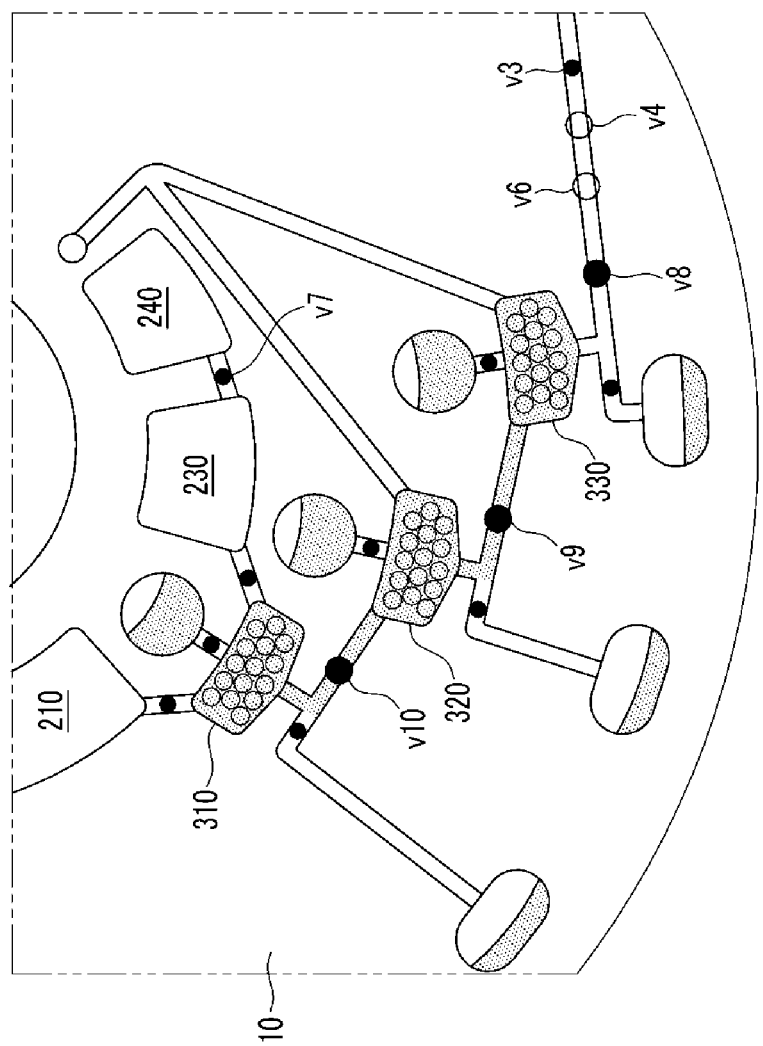

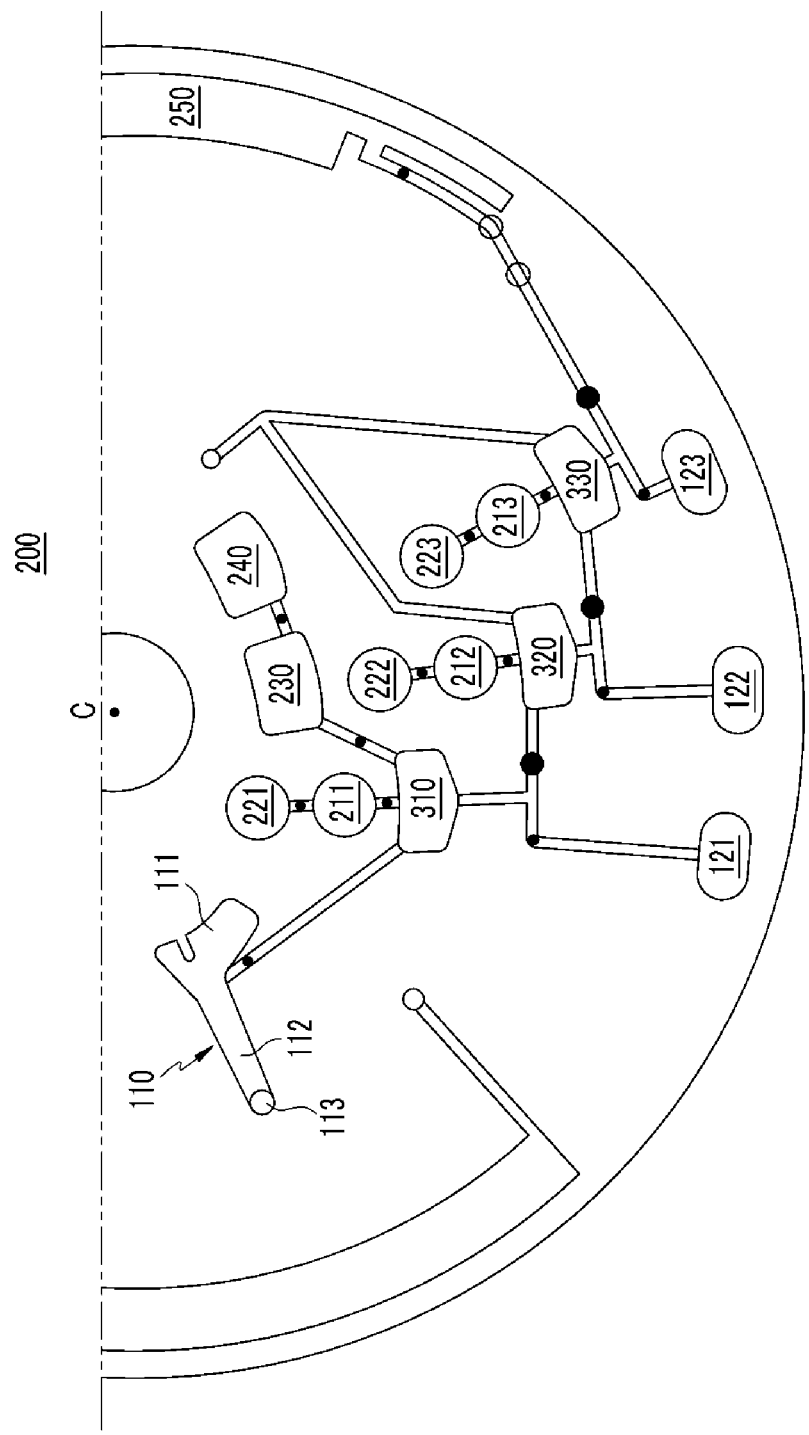

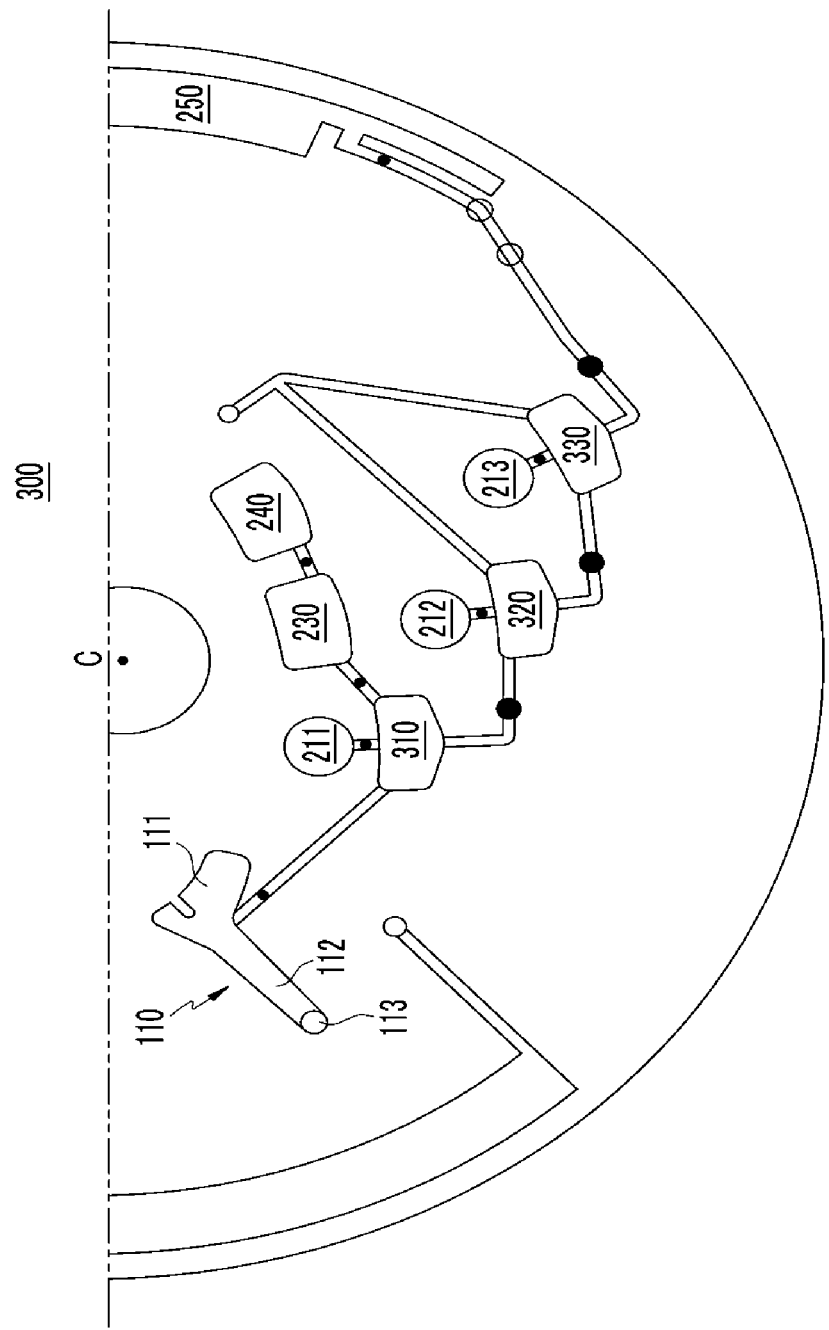

CENTRIFUGAL FORCE-BASED MICROFLUIDIC DEVICE AVAILABLE FOR RELIABILITY VERIFICATION, AND ANALYZING METHOD USING THE SAME

CROSS-REFERENCE TO RELATED APPLICATION

This application claims priority to and the benefit of Korean Patent Application No. 10-2011-0077505 filed in the Korean Intellectual Property Office on Aug. 3, 2011, the entire contents of which are incorporated herein by reference.

BACKGROUND OF THE INVENTION (a) Field of the Invention

The present invention relates to a centrifugal force-based microfluidic device capable of performing an immunological test, a genetic test, a biochemical test, environmental pollutant analysis, and the like, and an analysis method using the same.

(b) Description of the Related Art

A microfluidic device includes a plurality of chambers each storing a small amount of fluid, valves controlling fluid flow between the chambers, and various functional units each performing a designated function upon receiving a fluid.

A lab-on-a-chip is a chip including a microfluidic device, and several steps of reactions and manipulations may be performed thereon. In particular, a lab-on-a-chip using centrifugal force as a driving pressure for separating a sample and transferring a fluid is called a lab-on-a-disc.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a centrifugal force-based microfluidic device having an advantage of verifying analysis reliability, and an analyzing method using the same.

An exemplary embodiment of the present invention provides a microfluidic device including a platform and a microfluidic structure including a plurality of chambers formed within the platform and valves positioned between the chambers. The microfluidic structure includes a plurality of reaction chambers accommodating two or more types of markers specifically reacting with different types of target materials, separately by type. At least one of the target materials is a standard material, and at least one of the markers is a standard marker specifically reacting with the standard material.

The standard material may include at least one of a positive standard material and a negative standard material. Each of the plurality of reaction chambers may accommodate a reaction mediator with markers coated thereon.

The plurality of reaction chambers may be connected or isolated at some of stages of a reaction. The platform may be divided into a plurality of areas, and the microfluidic structure may be provided at each of the plurality of areas and independently operates.

The microfluidic structure may include a sample separation chamber. The sample separation chamber may include a sample collection unit formed to be parallel to a circumferential direction of the platform, and a sediment collection unit connected to the sample collection unit and formed to be parallel to a radial direction of the platform.

The plurality of reaction chambers may include a first reaction chamber which is first provided with a sample and a last reaction chamber that is provided with the sample last. The microfluidic structure may include a first storage chamber positioned in front of the first reaction chamber and accommodating one or more types of detection probes and a standard material.

The first storage chamber may be connected to the first reaction chamber through a normally closed valve, and the plurality of reaction chambers may be positioned to be farther than the first storage chamber from a rotation center of the platform. The plurality of reaction chambers may be connected through normally open valves so as to be sequentially provided with a mixture of the detection probe and the standard material from the first storage chamber.

The microfluidic structure may include a plurality of second storage chambers connected to the plurality of reaction chambers through normally closed valves and accommodating a substrate solution, respectively. The plurality of reaction chambers may be isolated as the normally open valves are closed after the coupling reaction between the target materials and the markers, and may be provided with the substrate solution from the plurality of second storage chambers, respectively.

The microfluidic structure may include a plurality of first storage chambers connected to the plurality of reaction chambers and accommodating one or more types of detection probes and the standard material, separately by type, respectively.

The plurality of first storage chambers may accommodate a detection probe to which at least one of a fluorescence material and a chemiluminescence material is bonded, and a standard material to which at least one of a fluorescence material and a chemiluminescence material is bonded.

The microfluidic structure may include a plurality of second storage chambers connected to the plurality of first storage chambers and accommodating a substrate solution, respectively.

The microfluidic structure may include a third storage chamber connected to the first reaction chamber through a normally closed valve and accommodating a cleansing solution. The microfluidic structure may include a fourth storage chamber connected to the third storage chamber through a normally closed valve and accommodating a cleansing solution.

The microfluidic structure may include a fifth storage chamber connected to the last reaction chamber and accommodating a residual solution. One normally closed valve, two reversible normally open valves, and one normally open valve may be installed between the last reaction chamber and the fifth storage chamber.

The microfluidic structure may include a plurality of detection chambers connected to the plurality of reaction chambers through normally closed valves and accommodating a stop solution, respectively.

Another embodiment of the present invention provides a multiplexed analysis method using a microfluidic device, including: transferring a sample to a first storage chamber accommodating a mixture of a detection probe and a standard material; sequentially transferring the mixture within the first storage chamber to a plurality of reaction chambers accommodating two or more types of markers specifically reacting with different types of target materials, separately by type, and performing an incubation reaction; discharging impurities, excluding target materials coupled to markers and detection probes, among the mixture within the reaction chambers; isolating the reaction chambers and supplying a substrate solution to the reaction chambers; and transferring the mixture within the reaction chambers to the detection chambers and measuring absorbance of the detection chambers. At least one of the target materials may be a standard material, and at least one of the markers may be a standard marker specifically reacting with a standard material. In the transferring of the mixture within the reaction chambers to the detection chambers and measuring of absorbance of the detection chambers, analysis reliability may be verified by analyzing a detection signal of the standard material.

Yet another embodiment of the present invention provides a multiplexed analysis method using a microfluidic device, including: sequentially transferring a sample to a plurality of reaction chambers accommodating two or more types of markers specifically reacting with different types of target materials, separately by type; transferring a detection probe and a standard material to the plurality of reaction chambers and performing an incubation reaction; discharging impurities, excluding target materials coupled to markers and detection probes, among the mixture within the reaction chambers; isolating the reaction chambers and supplying a substrate solution to the reaction chambers; and transferring the mixture within the reaction chambers to the detection chambers and measuring absorbance of the detection chambers. At least one of the target materials may be a standard material, and at least one of the markers may be a standard marker specifically reacting with a standard material. In the transferring of the mixture within the reaction chambers to the detection chambers and measuring of absorbance of the detection chambers, analysis reliability may be verified by analyzing a detection signal of the standard material.

Still another embodiment of the present invention provides a multiplexed analysis method using a microfluidic device, including: sequentially transferring a sample to a plurality of reaction chambers accommodating two or more types of markers specifically reacting with different types of target materials, separately by type; transferring a fluorescence or chemiluminescence material-bonded detection probe or a fluorescence or chemiluminescence material-bonded standard material to the plurality of reaction chambers and performing an incubation reaction; discharging impurities, excluding target materials coupled to markers and detection probes, among the mixture within the reaction chambers; and measuring a fluorescence or illumination detection signal of the reaction chambers. At least one of the target materials may be a standard material, and at least one of the markers may be a standard marker specifically reacting with a standard material. In the measuring of a fluorescence or illumination detection signal of the reaction chambers, analysis reliability may be verified by analyzing a detection signal of the standard material.

BRIEF DESCRIPTION OF THE DRAWINGS

FIGS. 6A to 6I are partial enlarged views of the microfluidic device according to the first embodiment of the present invention illustrated to explain a target material analysis and a reliability verification method.

FIG. 9 is a schematic view of a microfluidic device according to a second embodiment of the present invention.

FIG. 10 is a schematic view of a microfluidic device according to a third embodiment of the present invention.

DETAILED DESCRIPTION OF THE EMBODIMENTS

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

Figure 1:
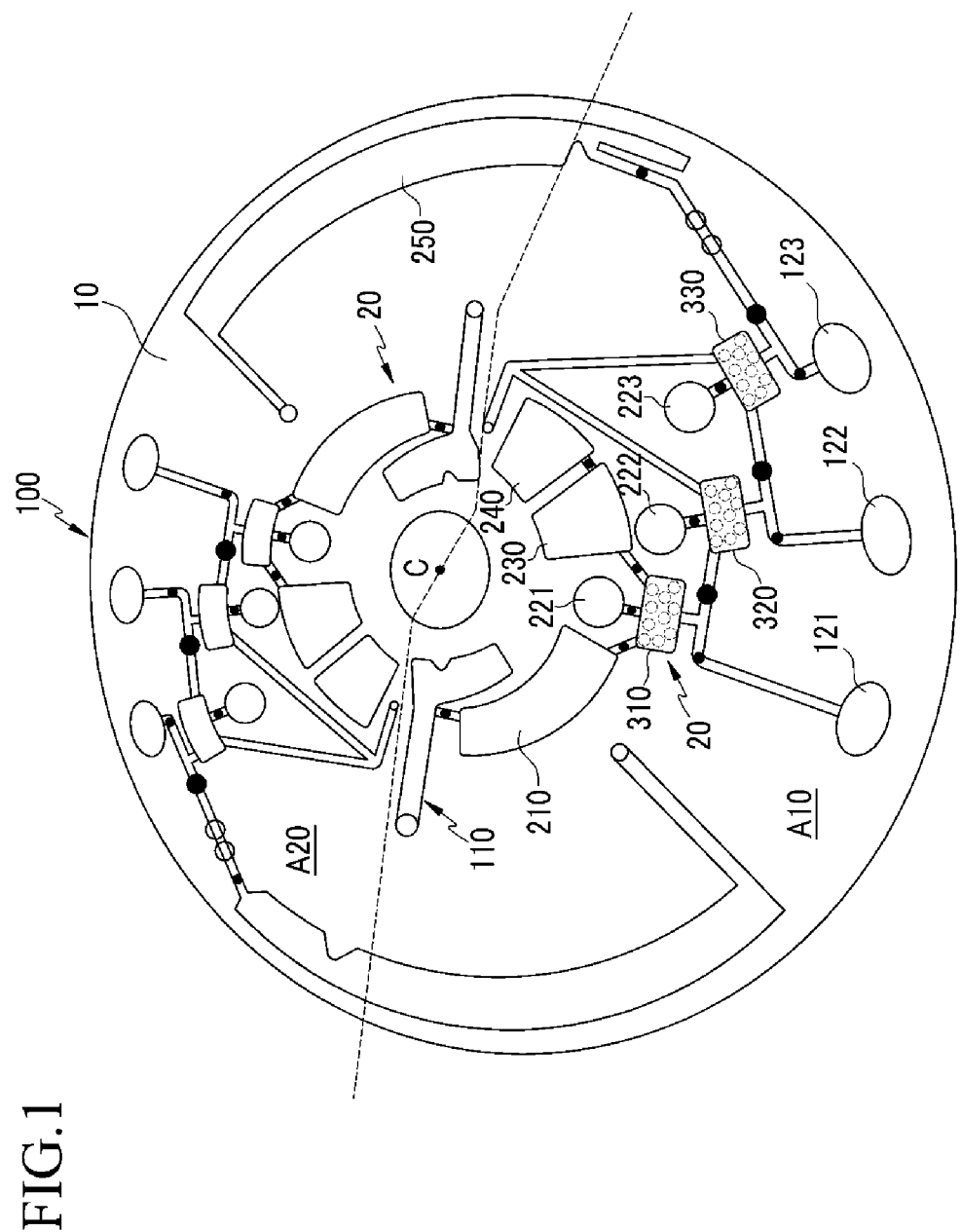
FIG. 1 is a schematic view of a microfluidic device according to a first embodiment of the present invention.

FIG. 1 is a schematic view of a microfluidic device according to a first embodiment of the present invention.

With reference to FIG. 1, a microfluidic device 100 according to a first embodiment of the present invention includes a rotatable disk type platform 10 and a microfluidic structure 20 formed within the platform 10. The microfluidic structure 20 includes chambers for accommodating a fluid and valves installed between chambers to control a fluid flow. The chambers may be connected to the valves by channels or may be directly connected to the valves without a channel.

The platform 10 has a rotation center and may be formed to have, for example, a disk-like shape. The platform 10 may be made of a plastic material that can be easily molded and has a biologically inactive surface, e.g., polystyrene (PS), polydimethylsiloxane (PDMS), polymethylmethacrylate (PMMA), polyacrylate, polycarbonate, polycyclic olefin, polyimide, polyurethane, or the like. Also, the platform 10 may be made of a material having chemical and biological stability and optical transparency.

The platform 10 may include a plurality of plates, e.g., an upper plate and a lower plate. The microfluidic structure 20 is formed to be intagliated on an inner face of the upper plate or the lower plate to provide chambers accommodating a fluid and valves controlling a fluid flow. The upper plate and the lower plate are bonded through various methods such as adhesion using an adhesive, ultrasonic joining (or ultrasonic fusion or welding), laser bonding, or the like, to constitute the microfluidic device 100.

The platform 10 is divided into a plurality of areas, and a microfluidic structure 20, which independently operates, is provided at each area. For example, the platform 10 may be divided into a first area A10 and a second area A20, and the microfluidic structure 20 for simultaneously detecting a plurality of target materials from a sample and verifying analysis reliability is provided at each of the first area A10 and the second area A20. In the present embodiment, the microfluidic structures 20 disposed at the first area A10 and the second area A20 have the same structure, so the microfluidic structure 20 disposed at the first area A10 will be described hereinafter.

Figure 2:
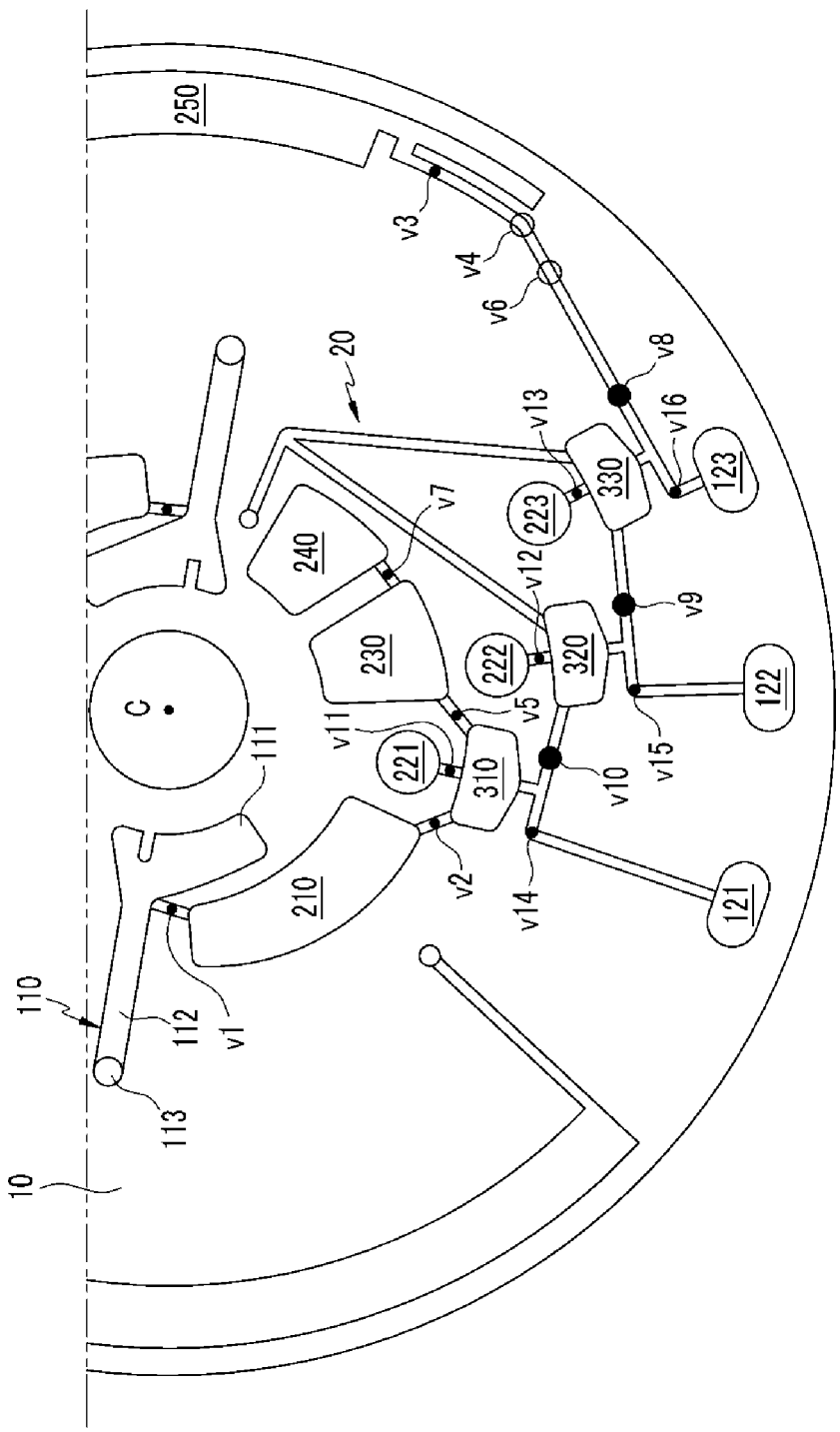
FIG. 2 is a partial enlarged view of the microfluidic device illustrated FIG. 1.

FIG. 2 is a partial enlarged view of the microfluidic device illustrated FIG. 1.

With reference to FIG. 2, the microfluidic structure 20 may include a sample separation chamber 110 connected to a sample injection hole 113. The sample separation chamber 110 provides a space accommodating a sample including a liquid, e.g., blood, saliva, urine, river water, a sample of soil, or the like.

The sample separation chamber 110 includes a sample collection unit 111 formed to be parallel to a circumferential direction of the platform 10, and a sediment collection unit 112 connected to the sample collection unit 111 and formed to be parallel to a radial direction of the platform 10. The sample injection hole 113 may be formed at an end portion of the sediment collection unit 112, and the sample collection unit 111 may be positioned to be closer than the sediment collection unit 112 to the rotation center C of the platform 10.

According to types of samples, the sample separation chamber 110 of the microfluidic structure 20 may be omitted, or a sediment liquid collected in the sediment collection unit 112 may be used as a sample.

The microfluidic structure 20 may include a first storage chamber 210 accommodating a mixture of one or more types of detection probes, one or more types of standard materials, and detection probes corresponding to the standard materials. The first storage chamber 210 is positioned to be farther than the sample collection unit 111 from the rotation center C of the platform 10. For example, when three reaction chambers 310, 320, and 330 are provided, the first storage chamber 210 may accommodate a mixture of two types of detection probes and one type of standard material, or may accommodate one type of detection probe and two different types of standard materials.

The mixture of the detection probes may be a conjugate mixture for an immunological test. For example, the microfluidic device 100 may be used to detect various proteins, e.g., C-reaction protein (CRT), cTn I (cardiac troponin I), NT-proBNP (N-terminal pro-B-type natriuretic peptide), and the like, for diagnosing a cardiovascular disease. In this case, the mixture of the detection probes may include at least one among anti-CRP, anti-cTn I, and anti-NT-proBNP to which HRP (horseradish peroxidase) is bonded.

A normally closed valve v1 is positioned between the sample collection unit 111 and the first storage chamber 210. When the normally closed valve v1 is opened, the first storage chamber 210 is connected with the sample collection unit 111. A channel may be formed between the sample collection unit 111 and the first storage chamber 210. The normally closed valve v1 shuts off fluid flow until it is opened upon receiving energy.

Figure 3:
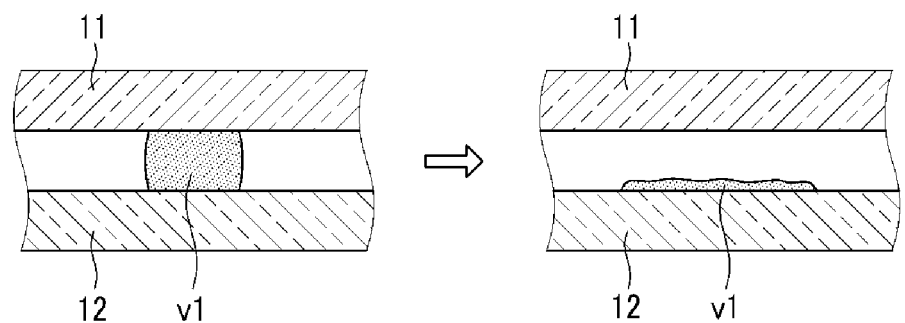
FIG. 3 is a schematic view showing an example of a normally closed valve of the microfluidic device illustrated in FIG. 2.

FIG. 3 is a schematic view showing an example of the normally closed valve.

With reference to FIG. 3, the normally closed valve v1 includes a valve material that exists in a solid state at room temperature to shut off the fluid flow. The valve material may include a heater material whose temperature is increased upon absorbing electromagnetic waves, and a material such as paraffin wax that can melt and coagulate according to temperature. When electromagnetic wave energy (laser, visible ray, infrared ray, or the like) is applied to the normally closed valve v1, the heater material instantaneously melts the paraffin wax to change the normally closed valve v1 into an opened state, and the valve material re-coagulates in the opened state.

In FIG. 3, reference numeral 11 denotes the upper plate of the platform 10, and 12 denotes the lower plate of the platform 10.

With reference back to FIG. 2, the microfluidic structure 20 includes a plurality of reaction chambers 310, 320, and 330 each including two or more types of markers specifically reacting different types of target materials. The two or more types of markers are separately installed in the plurality of reaction chambers 310, 320, and 330 according to the types. Here, one of the target materials is a standard material, and one of the markers is a standard marker specifically reacting with the standard material. The plurality of reaction chambers 310, 320, and 330 may be configured to include a corresponding marker or the standard marker directly coated thereon, or may accommodate reaction mediators such as a bead with a marker or the standard marker coated thereon.

Here, the "target material", which is an object material desired to be analyzed from the sample, may be, for example, a molecule-level material constituting a living body. The target material includes, for example, a protein, an antigen, an antibody, an enzyme, DNA, RNA, a hormone, a chemical material, and the like.

A "marker" refers to a material particularly reacting with a target material to capture the target material. For example, a marker may make a protein interaction, an antigen-antibody reaction, an enzyme-substrate reaction, a sequence-specific reaction, or the like, with a target material. As the two or more types of markers installed in mutually different reaction chambers, those that do not have cross-reactivity are used.

"Cross reactivity" refers to when a marker reacts to be bonded with two or more types of target materials, wherein the marker reacts to both the target material specific to the material and also to a material having a similar structure or having a partially same structure The two or more types of markers installed in the plurality of reaction chambers 310, 320, and 330 must specifically react to corresponding target materials and must not have cross-reactivity with each other.

A "standard material" may be a material that has physical properties similar to those of a material desired to be analyzed from a sample but does not exist in the sample. For example, a standard material may be a molecule-level material constituting a living body. A standard material includes, for example, a protein, an antigen, an antibody, an enzyme, DNA, RNA, a hormone, a chemical material, and the like.

Also, as the "standard marker", one that does not have cross-reactivity with one or more types of markers accommodated in different reaction chambers is used. In the present embodiment, the standard material may be a positive standard material.

When the microfluidic device 100 is used for an immune serum test, a bead on which a capture antibody is coated may be used, and when the microfluidic device 100 is used for gene analysis, a bead on which a corresponding genetic material is coated may be used. Also, when the microfluidic device 100 is used for an immune serum test, various materials such as an aptamer, or the like, may be used. Also, when the microfluidic device 100 is used for an immune serum test, a bead on which an antibody specifically reacting with the target material is coated and a bead on which an antibody specifically reacting with the standard material is coated may be used.

The reaction mediator configured as a bead has advantages in that it can be conveniently used, a mixed reaction is effective, and various types of target reactions are easily made, and here, the reaction mediator is not limited to the foregoing bead but includes a case in which a captured material specifically reacting with a target material is directly fixed to the surface of the reaction chambers 310, 320, and 330.

The number of the reaction chambers 310, 320, and 330 is equal to the number of target materials desired to be detected. The reaction chambers 310, 320, and 330 may include a first reaction chamber 310, a second reaction chamber 320, and a third reaction chamber 330. In FIG. 2, three reaction chambers 310, 320, and 330 are illustrated, but the number of the reaction chambers 310, 320, and 330 is not limited thereto.

A first bead coated with a standard marker is positioned at any one (e.g., the first reaction chamber 310) of the three reaction chambers 310, 320, and 330, and a second bead coated with a marker I is positioned at another (e.g., the second reaction chamber 320) of the three reaction chambers 310, 320, and 330. A third bead coated with a marker II is positioned at the remaining reaction chamber (e.g., the third reaction chamber 330). The first to third beads may be plastic beads, e.g., polystyrene (PS) or glass beads, and may have a micrometer size.

When the microfluidic device 100 is used for detecting various target proteins for diagnosing a cardiovascular disease, the marker I may be any one of a CRP capture antibody, a cTn I capture antibody, and an NT-proBNP capture antibody, and marker II may be any other of the CRP capture antibody, the cTn I capture antibody, and the NT-proBNP capture antibody. The types of markers may not be limited to the foregoing examples, and may vary depending on the type of target protein.

As the standard material, an antibody that does not exist in human blood, e.g., mouse IgG, or the like, may be used with a determined concentration, and as the standard marker, anti-IgG may be used. The types of the standard materials and standard markers are not limited to the foregoing examples.

The plurality of reaction chambers 310, 320, and 330 are positioned to be farther than the first storage chamber 210 from the rotation center C of the platform 10. The first reaction chamber 310, the second reaction chamber 320, and the third reaction chamber 330 in this order may be positioned to be closer to the first storage chamber 210. A normally closed valve v2 is positioned between the first storage chamber 210 and the first reaction chamber 310.

The plurality of reaction chambers 310, 320, and 330 may be maintained to be connected by normally open valves in an initial state before a sample is input. Namely, a normally open valve v10 may be positioned between the first reaction chamber 310 and the second reaction chamber 320, and a normally open valve v9 may be positioned between the second reaction chamber 320 and the third reaction chamber 330. The normally open valves v10 and v9 are open between the chambers to allow a fluid to flow until they are shut off upon receiving energy from the outside.

Meanwhile, the plurality of reaction chambers 310, 320, and 330 may be maintained in an independent state by normally closed valves in the initial state before the sample is input, and then, may be connected in some steps during a reaction. In this case, normally closed valves are positioned between the reaction chambers 310, 320, and 330.

Figure 4:
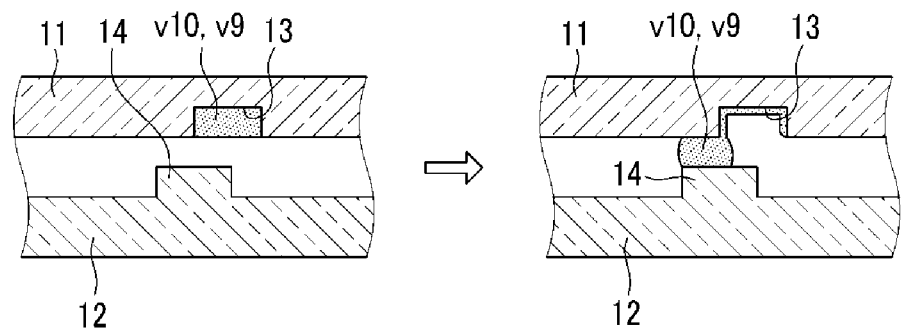
FIG. 4 is a schematic view showing an example of a normally open valve of the microfluidic device illustrated in FIG. 2.

FIG. 4 is a schematic view showing an example of normally open valves.

With reference to FIG. 4, a concave portion 13 and a convex portion 14 are positioned within the platform 10 in which normally open valves v10 and v9 are installed, and the concave portion 13 is filled with a valve material to open between the chambers. In FIG. 4, a case in which the concave portion 13 is positioned on the upper plate 11 of the platform 10 and the convex portion 14 is positioned on the lower plate 12 of the platform 10 is illustrated, but the opposite case can be also available. Central positions of the concave portion 13 and the convex portion 14 may be inconsistent, rather than coinciding.

The valve material may be the same as the valve material described above with respect to the normally closed valve. When electromagnetic wave energy is applied to the concave portion 13 of the normally open valves v10 and v9, the valve material may be melted to move from the concave portion 13 to the convex portion 14 and then coagulate, shutting off between the chambers. The valve material re-coagulates in the closed state.

With reference back to FIG. 2, the microfluidic structure 20 includes a plurality of second storage chambers 221, 222, and 223 connected to the reaction chambers 310, 320, and 330, and accommodating a substrate solution, respectively. The second storage chambers 221, 222, and 223 are positioned to be closer than the reaction chambers 310, 320, and 330 connected thereto to the rotation center C of the platform 10.

The substrate solution serves to substrate-react with the result of a conjugate reaction to express a certain color, and color formation occurs in a color corresponding to the amount of the target materials according to the substrate reaction.

A normally closed valve v11 is positioned between the first reaction chamber 310 and the pertinent second storage chamber 221, and a normally closed valve v12 is positioned between the second reaction chamber 320 and the pertinent second storage chamber 222. A normally closed valve v13 is positioned between the third reaction chamber 330 and the pertinent second storage chamber 223. Channels may be formed between the plurality of reaction chambers 310, 320, and 330 and the pertinent second storage chambers 221, 222, and 223.

The microfluidic structure 20 may include a third storage chamber 230 connected to the first reaction chamber 310 and accommodating a cleansing solution, and a fourth storage chamber 240 connected to the third storage chamber 230 and accommodating a cleansing solution. The cleansing solution may be a solution for cleansing residues after the reaction between the target materials and the markers. When cleansing is required to be performed two or more times, the two chambers 230 and 240 accommodating a cleansing solution may be provided to repeatedly perform a cleansing operation on the reaction chambers 310, 320, and 330.

A normally closed valve v5 is positioned between the third storage chamber 230 and the first reaction chamber 310, and a normally closed valve v7 is positioned between the fourth storage chamber 240 and the third storage chamber 230. The third storage chamber 230 and the fourth storage chamber 240 may be positioned to be closer than the first reaction chamber 310 to the rotation center C. The first storage chamber 210, the third storage chamber 230, and the fourth storage chamber 240 may be positioned side by side along a circumferential direction of the platform 10.

The microfluidic structure 20 includes a fifth storage chamber 250 connected to the third reaction chamber 330 and accommodating a residual solution discarded from the reaction chambers 310, 320, and 330. The fifth storage chamber 250 is empty at the time of fabrication, and is formed to have an internal volume corresponding to an overall capacity of the sample, the mixture of the standard material and the detection probe, the substrate solution, and the cleansing solution.

The fifth storage chamber 250 is positioned to be farther than the third reaction chamber 330 from the rotation center C of the platform 10, and may be positioned at the outermost portion of the platform 10.

One normally closed valve v3, two reversible normally open valves v4 and v6, and one normally open valve v8, are positioned between the third reaction chamber 330 and the fifth storage chamber 250. The normally closed valve v3 is positioned to be close to the fifth storage chamber 250, and the normally open valve v8 is positioned to be close to the third reaction chamber 330. Two reversible normally open valves v4 and v6 are positioned between the normally closed valves v3 and v8.

Here, the "reversible normally open valve" refers to a valve that cannot be changed into a closed state again once it is changed from an open state into a closed state and then changed into an open state. Namely, the "reversible normally open valve" cannot be changed into an open state and closed state repeatedly several times. That is, the reversible normally open valve refers to a valve that can be available for only a single reversible open state conversion. In the present embodiment, the valve that is available for only a single reversible state conversion is used, but a valve that is available for reversible state conversion several times may also be used.

Figure 5:
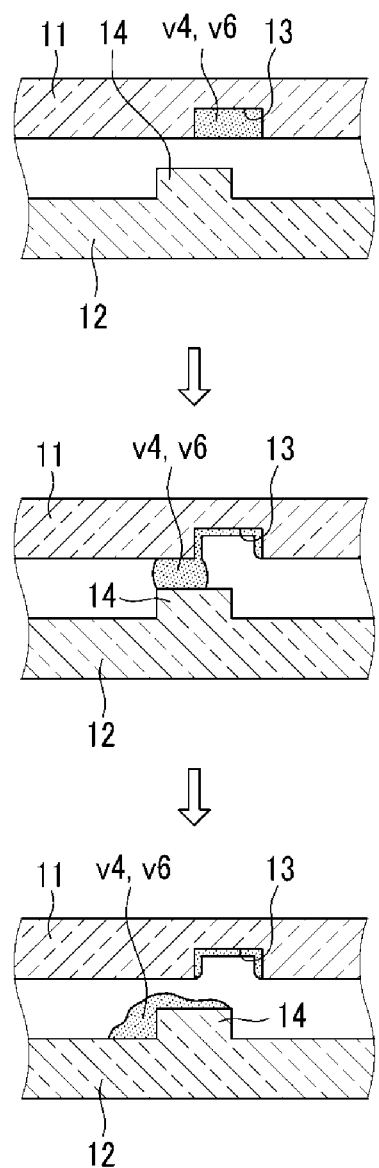
FIG. 5 is a schematic view showing an example of reversible normally open valves of the microfluidic device illustrated in FIG. 2.

FIG. 5 is a schematic view showing an example of the reversible normally open valves.

With reference to FIG. 5, a concave portion 13 and a convex portion 14 are positioned within the platform 10 where the reversible normally open valves v4 and v6 are installed, and the concave portion 13 is filled with a valve material to open between the chambers. The valve material may be the same as the valve material described above with respect to the normally open valves. When electromagnetic wave energy is applied to the concave portion 13, the valve material may be melted to move from the concave portion 13 to the convex portion 14 and then coagulate, shutting off between the chambers, and this process is the same as that of the foregoing normally open valves.

In the reversible normally open valves v4 and v6, electromagnetic wave energy is applied again to the valve material coagulated on the convex portion 14. Then, the valve material is melted again to flow along the side of the convex portion 14, opening between the chambers, and the valve material re-coagulates in the open state. Thus, the reversible normally open valves v4 and v6 have characteristics in which they are opened, closed, and then returned to the opened state.

With reference back to FIG. 2, the microfluidic structure 20 includes a plurality of detection chambers 121, 122, and 123 connected to the reaction chambers 310, 320, and 330, and accommodating a final reactant, respectively. The detection chambers 121, 122, and 123 are chambers in which absorbance is measured, and the concentration of the target materials, i.e., the specimens, can be calculated through the absorbance measurement. A stop solution for stopping the substrate reaction is accommodated in advance in the plurality of detection chambers 121, 122, and 123.

The detection chambers 121, 122, and 123 are positioned to be farther than the reaction chambers 310, 320, and 330 connected thereto from the rotation center C of the platform 10. The detection chambers 121, 122, and 123 may be positioned to be parallel to the fifth storage chamber 250 along the circumferential direction of the platform 10.

A normally closed valve is positioned between the first reaction chamber 310 and the first detection chamber 271, and a normally closed valve v15 is positioned between the second reaction chamber 320 and the second detection chamber 122. A normally closed valve v16 is positioned between the third reaction chamber 330 and the third detection chamber 123.

In FIG. 2, small black circles represent normally closed valves, large black circles represent normally open valves, and ring shapes represent reversible normally open valves.

In the microfluidic device 100 according to the present embodiment, a mixture of two or more types of detection probes and one type of standard material are accommodated in the first storage chamber 210, and two or more types of markers (including the standard marker) specifically reacting with different types of target materials (including the standard material) are installed in the plurality of reaction chambers 310, 320, and 330, separately by type. Here, the reaction chambers 310, 320, and 330 are connected by the normally open valves v10 and v9.

Accordingly, the mixture of the detection probes and the standard material accommodated in the first storage chamber 210 can be transferred to the reaction chambers 310, 320, and 330 within a short time by virtue of a single centrifugal force operation, and the overall reaction time can be shortened.

Also, the microfluidic device 100 according to the present embodiment can perform a multiplexed analysis of simultaneously detecting a plurality of target materials from a single sample, and can verify analysis reliability from a detection signal of the standard material. That is, when the detection signal of the standard material is determined to be normal, the analysis results of the target materials performed in the microfluidic device 100 can be trusted.

Hereinafter, a method for analyzing a target material and verifying reliability using the foregoing microfluidic device will be described in detail with reference to FIGS. 6A to 6I.

Figure 6A:
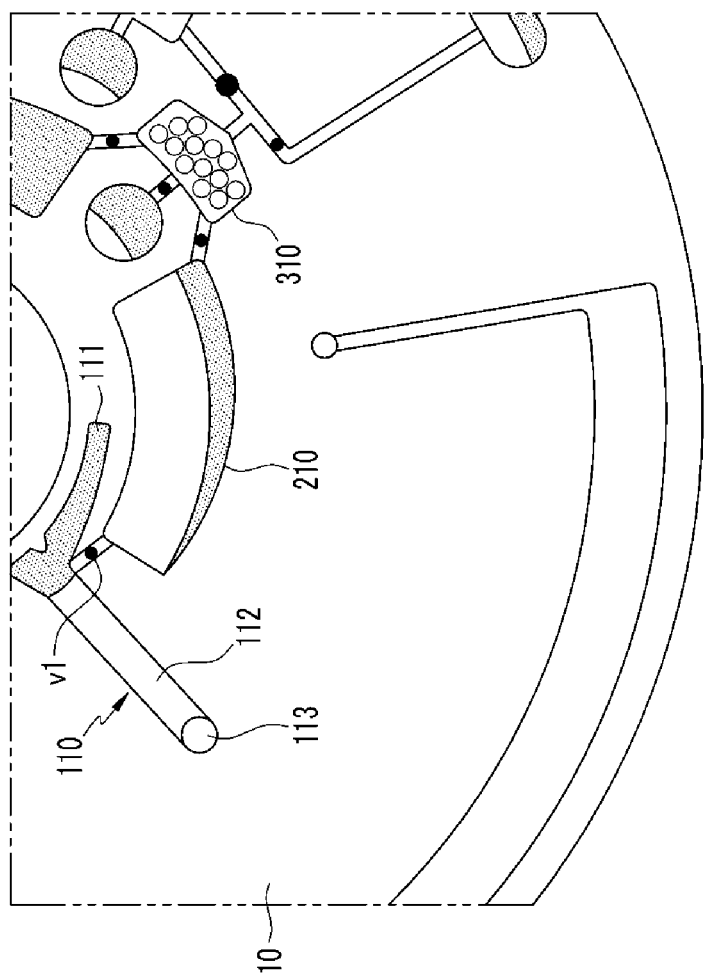

With reference to FIG. 6A, a sample in a fluid state is input to the sample separation chamber 110 through the sample injection hole 113, and the platform 10 is rotated at a high speed to generate centrifugal force. A weighty sediment among the sample is moved to the sediment collection unit 112 by the centrifugal force, and the other remaining component is moved to the sample collection unit 111, thus being separated.

The first storage chamber 210 is isolated from the sample separation chamber 110 by the normally closed valve v1, and a mixture of two types of detection probes, one type of standard material, e.g., a positive standard material, and a detection probe corresponding to the positive standard material, are accommodated in advance in the first storage chamber 210.

With reference to FIG. 6B, the normally closed valve v1 is opened by applying electromagnetic energy thereto, and the platform 10 is rotated to generate centrifugal force. Then, the sediment-removed sample is transferred to the first storage chamber 210 so as to be mixed with the mixture of two types of detection probes, one type of standard material, and the detection probe corresponding to the standard material.

With reference to FIG. 6C, the normally closed valve v2 is opened by applying electromagnetic energy thereto, and the platform 10 is rotated to generate centrifugal force. The mixture of the first storage chamber 220 is transferred to the first reaction chamber 310, the second reaction chamber 320, and the third reaction chamber 330 in this order by the centrifugal force to fill the first, second, and third reaction chambers 310, 320, and 330.

Here, the first, second, and third reaction chambers 310, 320, and 330 are connected by the normally open valves v10 and v9, so the mixture can be quickly transferred to all of the first, second, and third reaction chambers 310, 320, and 330 by a single centrifugal force operation. An incubation reaction is performed in the first, second, and third reaction chambers 310, 320, and 330 for about 10 minutes. The incubation reaction refers to a coupling reaction (or a fixation reaction) between the target materials, the markers, and the detection probes, and a coupling reaction between the standard material, the standard marker, and the detection probes.

Figure 6D:
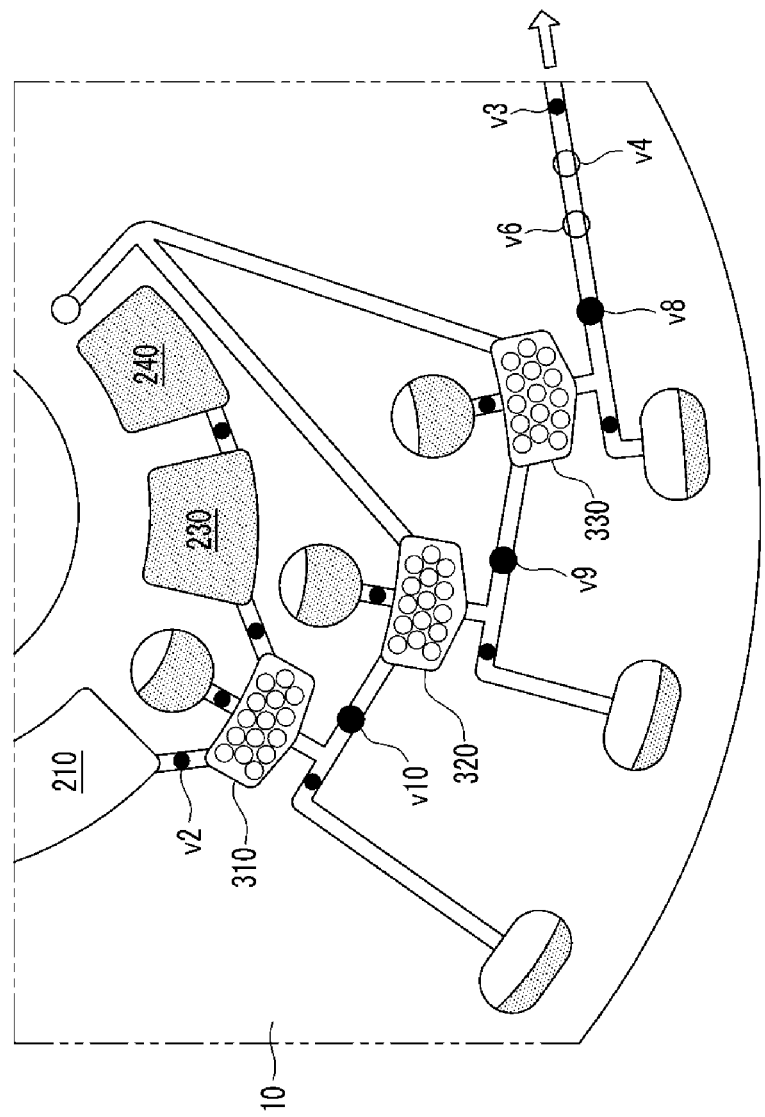

With reference to FIG. 6D, the normally closed valve v3 is opened by applying electromagnetic energy thereto, and the platform 10 is rotated to generate centrifugal force. Then, impurities, excluding the detection probe and the standard material combined with the standard marker and the detection probe and the specimen reacting with the marker in the first, second, and third reaction chambers 310, 320, and 330, are transferred to and accommodated in the fifth storage chamber 250 (See FIG. 2)

After the impurities are discharged, electromagnetic wave energy is applied to the reversible normally open valve v4 to change it into a closed state.

With reference to FIG. 6E, energy is applied to the normally closed valve v5 to open the normally closed valve v5, and the platform 10 is rotated to generate centrifugal force. The cleansing solution accommodated in the third storage chamber 230 is transferred by the centrifugal force to the first reaction chamber 310, the second reaction chamber 320, and the third reaction chamber 330 in this order to fill the first, second, and third reaction chambers 310, 320, and 330.

The reaction mediator of the first, second, and third reaction chambers 310, 320, and 330 is cleansed by using the cleansing solution, and then the reversible normally open valve v4 is changed into an opened state. Thereafter, the platform 10 is rotated to discharge the cleansing solution and the reaction impurities within the first, second, and third reaction chambers 310, 320, and 330 to the fifth storage chamber 250 (See FIG. 2). Electromagnetic wave energy is applied to the reversible normally open valve v6 to change it into a closed state.

With reference to FIG. 6F, energy is applied to the normally closed valve v7 to open the normally closed valve v7, and the platform 10 is rotated to generate centrifugal force. The cleansing solution accommodated in the fourth storage chamber 240 is transferred by the centrifugal force to the third storage chamber 230, the first reaction chamber 310, the second reaction chamber 320, and the third reaction chamber 330 in this order to fill the first, second, and third reaction chambers 310, 320, and 330.

Figure 6G:
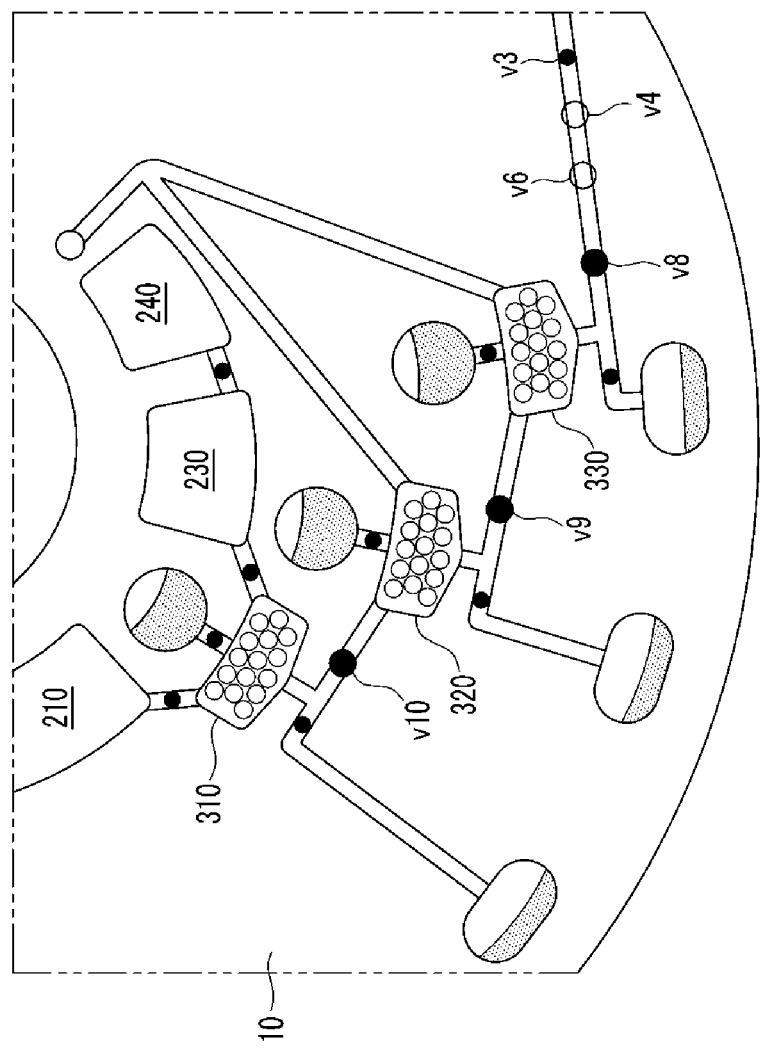

With reference to FIG. 6G, the reaction mediator of the first, second, and third reaction chambers 310, 320, and 330 is secondarily cleansed by using the cleansing solution, and then the reversible normally open valve v6 is changed into an opened state. Thereafter, the platform 10 is rotated to discharge the cleansing solution and the reaction impurities within the first, second, and third reaction chambers 310, 320, and 330 to the fifth storage chamber 250 (See FIG. 2), and energy is applied to the normally open valve v8 to close the normally open valve v8. Since the cleaning process is performed twice, detection precision can be enhanced.

Figure 6H:
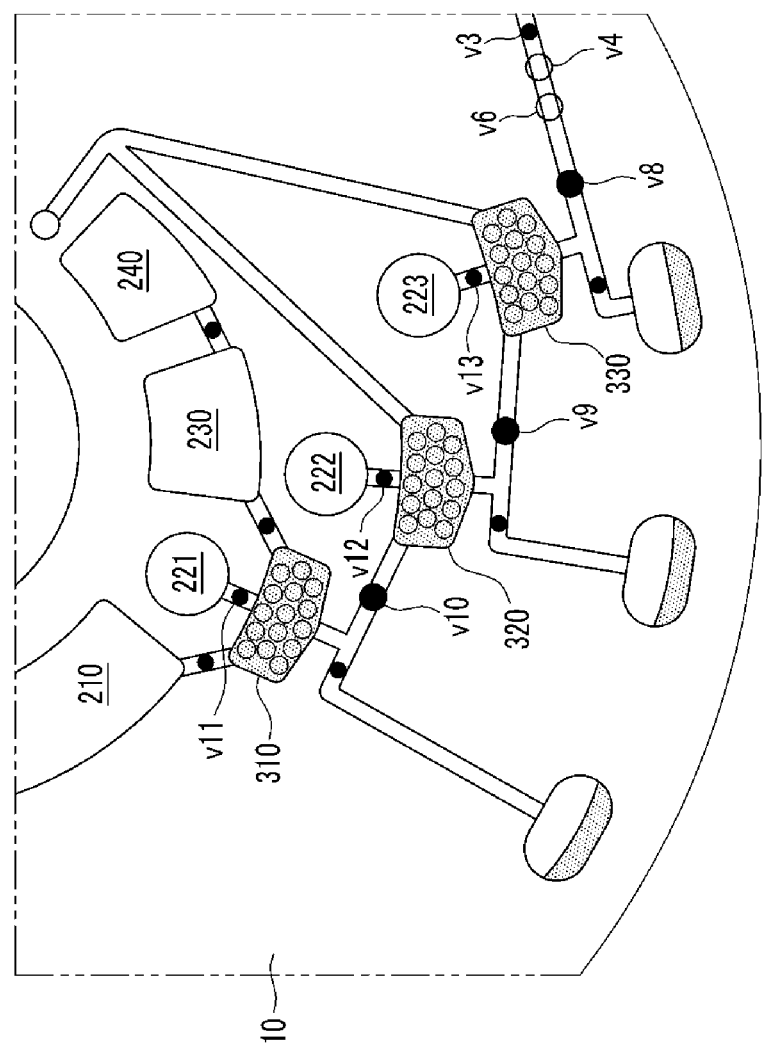

With reference to FIG. 6H, energy is applied to the normally open valve v10 and the normally open valve v9 to change them into a closed state, thus isolating the plurality of reaction chambers 310, 320, and 330.

Thereafter, energy is applied to the normally closed valve v11, the normally closed valve v12, and the normally closed valve v13 to open them. Then, the platform 10 is rotated to apply centrifugal force. The substrate solution accommodated in advance in the second storage chambers 221, 222, and 223 is transferred by the centrifugal force to the first, second, and third reaction chambers 310, 320, and 330, respectively.

The substrate solution transferred to the first, second, and third reaction chambers 310, 320, and 330 is mixed with the result of the reaction between the markers and the target materials within the respective first, second, and third reaction chambers 310, 320, and 330, and the mixture within the respective first, second, and third reaction chambers 310, 320, and 330 is expressed in a color corresponding to the amounts of the specimens (target materials) and the standard material according to the substrate reaction.

Figure 6I:
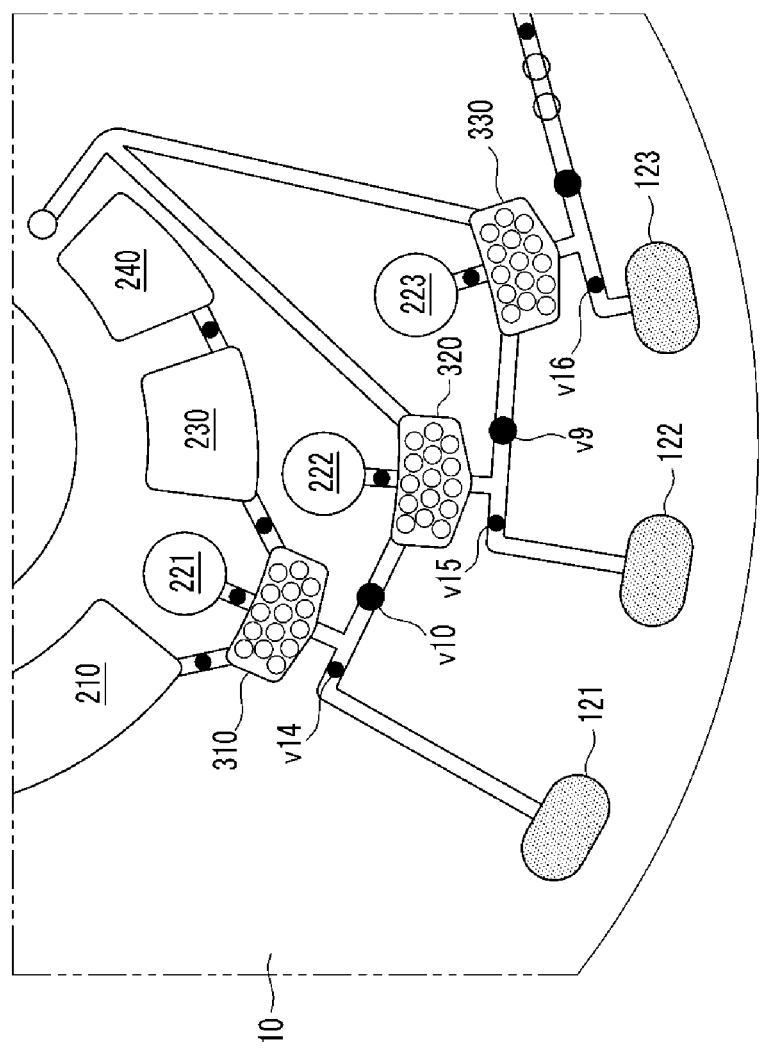

With reference to FIG. 6I, energy is applied to the normally closed valve v14, the normally closed valve v15, and the normally closed valve v16 to open them, and the platform 10 is rotated to apply centrifugal force. The mixture within the first, second, and third reaction chambers 310, 320, and 330 is transferred by the centrifugal force to the plurality of detection chambers 121, 122, and 123 in which the stop solution is accommodated in advance. The stop solution is mixed with the mixtures transferred from the first, second, and third reaction chambers 310, 320, and 330, terminating the substrate reaction.

Subsequently, absorbance of the detection chambers 121, 122, and 123 is measured by using a measurement device (not shown) including a light emitting diode (LED) and a photodiode. The measurement device includes a controller having a data storage and calculation function, and a display unit. The controller, which stores a reference absorbance in advance, compares the measured absorbance with the reference absorbance to calculate the concentration of the standard material and the target materials with respect to each of the detection chambers 271, 272, and 273, and outputs information regarding the concentration of the standard material and the target materials to the display unit. Meanwhile, the measurement device may output the information regarding the concentration of the target materials only when the concentration of the standard material satisfies a reference range, or otherwise, the measurement device may output an error message.

Figure 7:
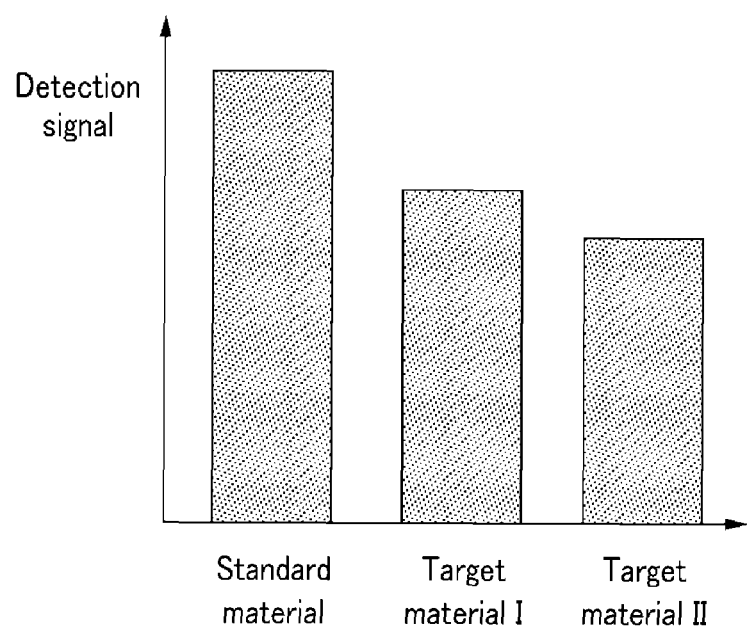
FIGS. 7 and 8 are graphs showing examples of detection signals that can be measured in detection chambers of the microfluidic device illustrated in FIG. 2.

FIG. 7 is a graph showing an example of detection signals that can be measured in a plurality of detection chambers.

With reference to FIG. 7, when a detection signal value of a positive standard material satisfies a reference range, the analysis results with respect to a target material I and a target material II can be trusted. Thus, analysis reliability with respect to the target materials I and II can be verified based on the detection signal of the standard material.

Meanwhile, in the above description, the mixture of two or more types of detection probes and one type of standard material are accommodated in the first storage chamber 210, but one type of detection probe and a mixture of two or more types of standard materials may be accommodated in the first storage chamber 210. In this case, the two or more types of standard materials may include a positive standard material and a negative standard material.

Also, any one (e.g., the first reaction chamber 310) of the plurality of reaction chambers 310, 320, and 330 accommodates a standard marker specifically reacting with the positive standard material and another (e.g., the second reaction chamber 320) of the plurality of reaction chambers 310, 320, and 330 accommodates a standard marker specifically reacting with a negative standard material. Also, the other remaining reaction chamber (e.g., the third reaction chamber 330) accommodates a marker specifically reacting with a target material.

The plurality of reaction chambers 310, 320, and 330 may be configured to include the corresponding standard marker directly coated thereon or may accommodate reaction mediators such as beads with the standard marker or the markers coated thereon.

Figure 8:
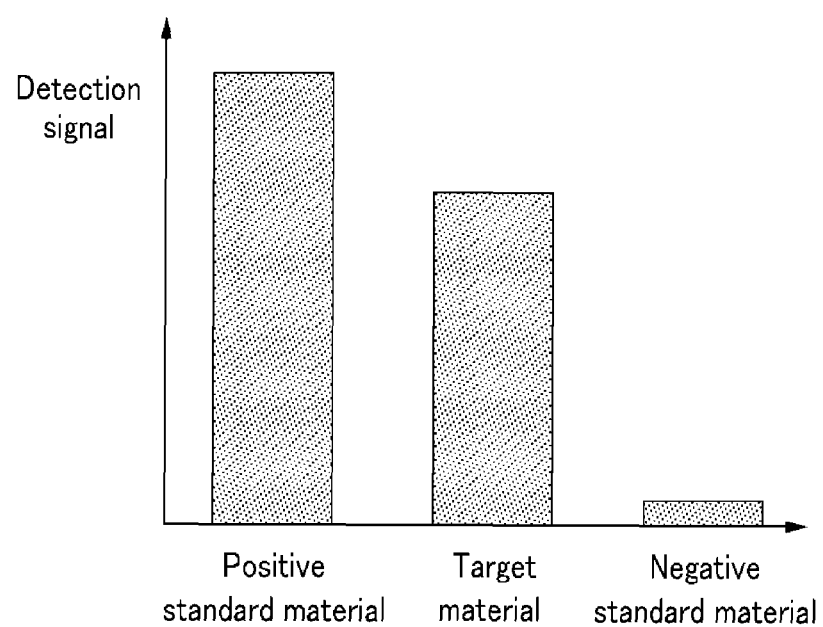

FIG. 8 is a graph showing an example of detection signals that can be measured in the plurality of detection chambers in the foregoing case.

With reference to FIG. 8, when a detection signal value of a positive standard material and that of a negative standard material satisfy a reference range, the analysis results with respect to a target material can be trusted. Thus, analysis reliability with respect to the target material can be verified based on the detection signals of the positive and negative standard materials.

Four or more reaction chambers may be provided. In this case, the first storage chamber 210 may accommodate a mixture of two or more types of standard materials and a mixture of two or more types of detection probes. The plurality of reaction chambers may accommodate a standard marker specifically reacting with a positive standard material, a standard marker specifically reacting to a negative standard material, and two or more types of markers specifically reacting with different types of target materials, separately by type.

In this case, the microfluidic device 100 can simultaneously detect a plurality of target materials, and verify the analysis reliability of the target materials with high efficiency by using the detection signals of the positive and negative standard materials.

FIG. 9 is a schematic view of a microfluidic device according to a second embodiment of the present invention.

With reference to FIG. 9, a microfluidic device 200 according to a second embodiment of the present invention has the same configuration as that of the first embodiment as described above, except that a plurality of first storage chambers 211, 212, and 213 are individually installed at the plurality of reaction chambers 310, 320, and 330. That is, the same number of first storage chambers 211, 212, and 213 as that of the reaction chambers 310, 320, and 330 are provided.

The plurality of first chambers 211, 212, and 213 are installed between the second storage chambers 221, 222, and 223 and the respective reaction chambers 310, 320, and 330. Normally closed valves are installed between the second storage chambers 221, 222, and 223 and the first storage chambers 211, 212, and 213, and between the first storage chambers 211, 212, and 213 and the corresponding reaction chambers 310, 320, and 330.

The standard material corresponding to the standard marker and the detection probe or detection probes corresponding to the markers accommodated in the corresponding reaction chambers 310, 320, and 330 are accommodated in the plurality of storage chambers 211, 212, and 213, separately by type.

In the microfluidic device 200 according to the second embodiment of the present invention, a sample without a sediment is sequentially transferred to the reaction chambers 310, 320, and 330, and the target materials and the detection probes accommodated in advance in the plurality of storage chambers 211, 212, and 213 are transferred to the plurality of reaction chambers 310, 320, and 330 to perform an incubation reaction.

Impurities, excluding the standard material coupled with the standard marker and the detection probe and the target materials coupled with the markers and the detection probes in the mixture within the reaction chambers 310, 320, and 330, are discharged, the reaction chambers 310, 320, and 330 are isolated, and then a substrate solution accommodated in advance in the plurality of second storage chambers 221, 222, and 223 is supplied to the reaction chambers 310, 320, and 330. Subsequently, the mixture within the reaction chambers 310, 320, and 330 are transferred to the detection chambers 121, 122, and 123, and absorbance of the detection chambers 121, 122, and 123 is measured, thus performing both the target material analysis and the analysis reliability verification.

FIG. 10 is a schematic view of a microfluidic device according to a third embodiment of the present invention.

With reference to FIG. 10, a microfluidic device 300 according to a third embodiment of the present invention has the same configuration as that of the first embodiment, except that the second storage chambers and the detection chambers of the first embodiment are omitted and the plurality of first storage chambers 211, 212, and 213 accommodating a fluorescence material or a chemiluminescence material-bonded detection probe, or a fluorescence material or a chemiluminescence material-bonded standard material, are installed at the plurality of reaction chambers 310, 320, and 330, respectively.

In the third embodiment of the present invention, a fluorescence material or a chemiluminescence material, instead of the HRP (horseradish peroxidase) of the first embodiment, is bonded to the detection probes and the standard material accommodated in the first storage chambers 211, 212, and 213. In this case, the target materials and the standard material can be directly detected from the reaction chambers 310, 320, and 330 without having the second storage chambers storing a substrate solution and the detection chambers storing a stop solution.

The standard material corresponding to the standard marker and the detection probe accommodated in the corresponding reaction chambers 310, 320, and 330 or the detection probes corresponding to the markers are accommodated in the plurality of first storage chambers 211, 212, and 213, separately by type, and the respective target materials and the detection probes are transferred to the corresponding reaction chambers 310, 320, and 330 so as to be used in a reaction. Normally closed valves are installed between the first storage chambers 211, 212, and 213, and the corresponding chambers 310, 320, and 330.

In the microfluidic device 300 according to the third embodiment of the present invention, a sample without a sediment is sequentially transferred to the plurality of reaction chambers 310, 320, and 330, and the fluorescence material or chemiluminescence material-bonded detection probe, or the fluorescence material or chemiluminescence material-bonded standard material, stored in advance in the corresponding first storage chambers 211, 212, and 213 are transferred to the reaction chambers 310, 320, and 330, respectively, to perform an incubation reaction.

Impurities, excluding the standard material coupled with the standard marker, the target materials coupled with the markers, and the detection probe in the mixture within the reaction chambers 310, 320, and 330, are discharged, and then a fluorescence or illumination detection signal of the reaction chambers 310, 320, and 330 is measured, thus performing both a target material analysis and an analysis reliability verification.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A microfluidic device comprising:
a platform that can be rotated with respect to a rotation center; and
a microfluidic structure,
wherein the microfluidic structure comprises:
a sample separation chamber;
a plurality of reaction chambers serially located on the platform that are concentrically arranged outward from the rotation center and along the circumferential direction with respect to the rotation center;
at least one channel which connects the reaction chambers and has a normally open valve in an initial state;
a plurality of first reagent storage chambers, each of the first reagent storage chambers directly connected to one of the reaction chambers via a channel having a normally closed valve in an initial state; and
wherein the reaction chambers include different markers, the different markers specifically react with different target materials,
wherein one of the different markers is a control marker specifically reacting with a control material,
wherein the reaction chambers are sequentially provided with a sample.

2. The microfluidic device of claim 1, further comprising a plurality of detection chambers, wherein each of the detection chambers is connected to each of the reaction chambers via a normally closed valve in an initial state and located further from the rotation center than the reaction chamber connected to.

3. The microfluidic device of claim 1, further comprising a waste storage chamber connected to the reaction chamber furthest from the rotation center through a channel which comprises one normally closed valve in an initial state, two one-time reversible open valves from an initial state, and one normally open valve in an initial state.

4. The microfluidic device of claim 1, further comprising a first cleansing solution storage chamber connected to the reaction chamber nearest from the rotation center via a normally closed valve in an initial state, wherein the first cleansing solution storage chamber is located nearer from the rotation center than the reaction chambers.

5. The microfluidic device of claim 4, further comprising a second cleansing solution storage chamber connected to the first cleansing solution storage chamber via a normally closed valve in an initial state.

6. The microfluidic device of claim 1, further comprising a plurality of second reagent storage chambers connected to the first reagent storage chambers via normally closed valves in an initial state.

7. The microfluidic device of claim 6, wherein each of the second reagent storage chambers is located nearer from the rotation center than the first reagent storage chamber connected to.

8. The microfluidic device of claim 7, wherein each of the first reagent storage chambers is located nearer from the rotation center than the reaction chamber connected to.

9. The microfluidic device of claim 1, further comprising a first storage chamber interposed between the sample separation chamber and the reaction chamber nearest from the rotation center and configured to house one or more types of detection probes and the control material.

10. The microfluidic device of claim 9, wherein the first storage chamber is connected to the sample separation chamber and the reaction chamber nearest from the rotation center via normally closed valves in an initial state.

11. The microfluidic device of claim 1, wherein the reaction chambers comprise first, second and third reaction chambers, the first reaction chamber and the second reaction chamber are connected through a first channel having a normally open valve in an initial state and the second reaction chamber and the third reaction chamber are connected through a second channel having a normally open valve in an initial state.

12. The microfluidic device of claim 1, wherein the platform is divided into a plurality of areas, and the microfluidic structure is provided at each of the plurality of areas and independently operates.

13. The microfluidic device of claim 1, wherein the sample separation chamber comprises:
a sample collection unit formed to be parallel to a circumferential direction of the platform; and
a sediment collection unit connected to the sample collection unit and formed to be parallel to a radial direction of the platform,
wherein the sediment collection unit has a sample injection hole which is disposed at an end of the sediment collection unit opposite to the other end of the sediment collection unit to which the sample collection unit is connected.

* * * * *